United States Patent
Lee et al.

(10) Patent No.: US 11,590,383 B2
(45) Date of Patent: Feb. 28, 2023

(54) WEARABLE DEVICE AND EXERCISE SUPPORT METHOD PERFORMED BY THE WEARABLE DEVICE

(71) Applicant: Samsung Electronics Co., Ltd., Suwon-si (KR)

(72) Inventors: Youn Baek Lee, Yongin-si (KR); Jusuk Lee, Suwon-si (KR); Keehong Seo, Suwon-si (KR); Seungyong Hyung, Suwon-si (KR); Jungsik Hwang, Seoul (KR); Bokman Lim, Suwon-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 28 days.

(21) Appl. No.: 17/009,046

(22) Filed: Sep. 1, 2020

(65) Prior Publication Data

US 2021/0128972 A1    May 6, 2021

(30) Foreign Application Priority Data

Nov. 4, 2019    (KR) .................. 10-2019-0139447

(51) Int. Cl.
*A63B 21/00* (2006.01)
*A61B 5/11* (2006.01)
(Continued)

(52) U.S. Cl.
CPC .......... *A63B 21/4025* (2015.10); *A61B 5/112* (2013.01); *A61B 5/6812* (2013.01);
(Continued)

(58) Field of Classification Search
CPC ...... A61B 5/112; A61B 5/6812; B25J 9/0006; A63B 21/4011; A63B 21/4025;
(Continued)

(56) References Cited

U.S. PATENT DOCUMENTS 9,782,332 B2    10/2017    Ogawa et al.
2007/0054777 A1    3/2007    Kawai et al.
(Continued)

FOREIGN PATENT DOCUMENTS

JP    2002-301124 A    10/2002
KR    10-2017-0019175 A    2/2017
(Continued)

OTHER PUBLICATIONS

Malanga, Gerald and DeLisa, Joel. Clinical Observation. Dec. 24, 2012. Veteran's Health Administration Office of Research and Development. pp. 5-6. Retrieved from https://web.archive.org/web/20121224070043/https://www.rehab.research.va.gov/mono/gait/malanga.pdf (Year: 2012).*

(Continued)

*Primary Examiner* — Sundhara M Ganesan
(74) *Attorney, Agent, or Firm* — Harness, Dickey & Pierce, P.L.C.

(57) ABSTRACT

A wearable device and an exercise support method performed by the wearable device are disclosed. The exercise support method includes receiving exercise setting information associated with a lower body muscle that is selected by a user input, determining a torque profile to be applied to the wearable device based on the received exercise setting information, and operating an actuator of the wearable device based on the determined torque profile.

18 Claims, 8 Drawing Sheets

(51) Int. Cl.
    *A61B 5/00*     (2006.01)
    *B25J 9/00*     (2006.01)

(52) U.S. Cl.
    CPC ......... *A63B 21/4011* (2015.10); *B25J 9/0006* (2013.01); *A63B 2220/54* (2013.01); *A63B 2225/50* (2013.01)

(58) Field of Classification Search
    CPC ........ A63B 21/00178; A63B 21/00181; A63B 21/065; A63B 21/0059; A63B 21/4009; A63B 21/005; A63B 2220/54; A63B 2220/00; A63B 2225/50; A63B 2225/20; A63B 23/04; A63B 24/0062; A63B 24/0087; A63B 69/0028; A63B 2024/0065; A63B 71/06; A63B 71/0619; A63B 2071/0661; A61H 2201/5061; A61H 2201/1628; A61H 2201/164; A61H 2201/165; A61H 2201/5058; A61H 1/0244; A61H 2205/088; A61H 3/00
See application file for complete search history.

(56) References Cited

U.S. PATENT DOCUMENTS

| | | |
|---|---|---|
| 2010/0050765 A1 | 3/2010 | Kadota et al. |
| 2011/0004322 A1 | 1/2011 | Sankai |
| 2017/0027801 A1* | 2/2017 | Choi ..................... A61B 5/024 |
| 2017/0065441 A1* | 3/2017 | Lee ........................ A61F 2/70 |
| 2019/0046078 A1* | 2/2019 | Lim ..................... A61H 1/0237 |
| 2020/0289030 A1* | 9/2020 | Ikeuchi .................. A61F 5/028 |
| 2021/0121354 A1* | 4/2021 | Seo ................... A63B 23/0482 |
| 2021/0121729 A1* | 4/2021 | Kim .................... B25J 9/0006 |
| 2021/0162263 A1* | 6/2021 | Roh .................... A61B 5/1071 |

FOREIGN PATENT DOCUMENTS

| | | |
|---|---|---|
| KR | 10-2017-0083829 A | 7/2017 |
| KR | 10-2017-0107707 A | 9/2017 |
| WO | WO-2018/207108 A1 | 11/2018 |

OTHER PUBLICATIONS

Extended European Search Report dated Mar. 25, 2021, for corresponding EP Application No. 20205507.5.

* cited by examiner

WEARABLE DEVICE AND EXERCISE SUPPORT METHOD PERFORMED BY THE WEARABLE DEVICE

CROSS-REFERENCE TO RELATED APPLICATION

This application claims under 35 U.S.C. § 119 to Korean Patent Application No. 10-2019-0139447 filed on Nov. 4, 2019, in the Korean Intellectual Property Office, the entire contents of which are incorporated herein by reference in their entirety.

BACKGROUND

1. Field

At least one example embodiment relates to a wearable device and/or an exercise support method performed by the wearable device.

2. Description of the Related Art

A walking assist device may be generally used to assist a user who experiences inconvenience in walking. Such an inconvenience in walking may be attributed to various reasons, for example, diseases or accidents, and the user cannot walk readily on his/her own due to such reasons. In such a case, the walking assist device may be used to assist the user during a walking exercise as part of rehabilitation therapies. In addition, a recent issue of aging societies has contributed to a growing number of people who experience inconvenience and pain from reduced muscular strength or joint problems due to aging. Thus, there is a growing interest in walking assist devices that enable elderly users or patients with reduced muscular strength or joint problems to walk with less effort. A walking assist device may be worn on a body of a user, providing the user with power needed to walk and assisting the user with walking in a normal gait pattern.

SUMMARY

At least one example embodiment relates to an exercise support method performed by a wearable device.

In at least one example embodiment, the exercise support method may include receiving exercise setting information via an input, the exercise setting information indicating selected lower body muscles of a user to exercise; determining a torque profile to apply to the wearable device based on the exercise setting information; and operating an actuator of the wearable device based on the torque profile.

In at least one example embodiment, the determining of the torque profile comprises: setting the torque profile such that a resistance torque to hinder a movement of the user is output in one or more gait segments corresponding to the selected lower body muscles.

In at least one example embodiment, the determining of the torque profile comprises: determining a resistance torque application interval according to the exercise setting information based on a gait phase of the user, wherein the operating the actuator applies a resistance torque during the resistance torque application interval within one or more gait segments of the gait phase.

In at least one example embodiment, the exercise setting information includes information associated with the selected lower body muscles from among a plurality of lower body muscles of the user.

In at least one example embodiment, the receiving of the exercise setting information comprises receiving the exercise setting information from a remote controller configured to communicate with the wearable device.

In at least one example embodiment, the determining of the torque profile comprises: estimating a gait phase of the user based on sensor information sensed by one or more sensors of the wearable device; and determining the torque profile based on the gait phase and the exercise setting information.

In at least one example embodiment, the determining of the torque profile comprises: identifying one or more gait segments of the gait phase corresponding the selected lower body muscles; and setting the torque profile such that a resistance torque is supplied to the actuator in the one or more gait segments.

In at least one example embodiment, the determining of the torque profile comprises: determining the torque profile such that an assistance torque that supports a leg movement of the user is output in a first time interval and a resistance torque that hinders the leg movement of the user is output in a second time interval.

In at least one example embodiment, the wearable device is configured to operate in one of a walking assist mode and an exercise mode such that, in the walking assist mode the wearable device assists a leg movement of the user and, in the exercise mode the wearable device outputs a resistance torque to hinder the leg movement of the user.

At least one example embodiment relates to a non-transitory computer-readable medium comprising computer readable instructions that, when executed by a computer, cause the computer to perform the exercise support method.

At least one example embodiment relates to an exercise support method performed by a wearable device.

In at least one example embodiment, the exercise support method may include selectively setting the wearable device to an exercise mode; receiving exercise setting information via an input, the exercise setting information indicating selected lower body muscles of a user to exercise; and outputting, via an actuator of the wearable device, a resistance torque that hinders a movement of the user in one or more gait segments corresponding to the selected lower body muscles.

In at least one example embodiment, the outputting of the resistance torque comprises: setting a torque profile such that the resistance torque is output in the one or more gait segments corresponding to the selected lower body muscles; and outputting the resistance torque through the actuator based on the torque profile.

At least one example embodiment relates to a wearable device.

In at least one example embodiment, the wearable device may include an actuator configured to output a torque based on a torque profile; and a controller configured to: receive exercise setting information via an input, the exercise setting information indicating selected lower body muscles of a user to exercise, and determine the torque profile based on the exercise setting information.

In at least one example embodiment, the controller is configured to set the torque profile such that a resistance torque to hinder a movement of the user is output in one or more gait segments corresponding to the selected lower body muscles.

In at least one example embodiment, the wearable device further includes a sensor configured to sense a movement of the user to generate sensing information, wherein the controller is configured to: estimate a gait phase of the user based on the sensing information, and determine the torque profile based on the gait phase and the exercise setting information.

In at least one example embodiment, the controller is configured to, identify one or more gait segments of the gait phase corresponding to the selected lower body muscles, and set the torque profile such that a resistance torque is supplied to the actuator in the one or more gait segments.

In at least one example embodiment, the controller is configured to determine the torque profile such that an assistance torque that supports a leg movement of the user is output in a first time interval and a resistance torque that hinders the leg movement of the user is output in a second time interval.

In at least one example embodiment, the wearable device is configured to operate in one of a walking assist mode and an exercise mode such that, in the walking assist mode the wearable device assists a leg movement of the user and, in the exercise mode the wearable device outputs a resistance torque to hinder the leg movement of the user.

In at least one example embodiment, the wearable device further comprises a communicator configured to receive the exercise setting information from a remote controller.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
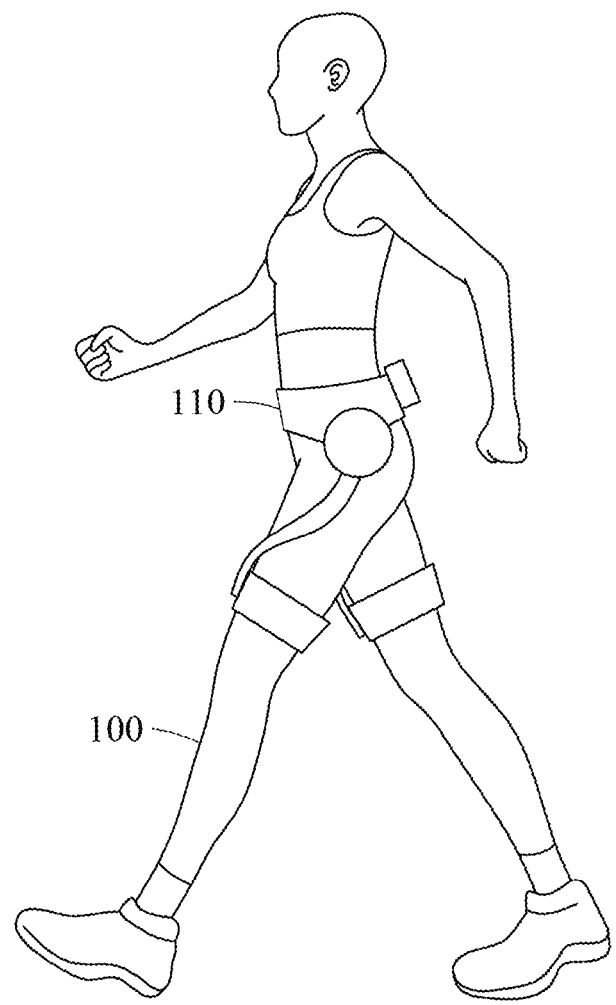
FIG. 1 is a diagram illustrating an example of a wearable device worn on a user according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

Hereinafter, examples will be described in detail with reference to the accompanying drawings, and like reference numerals in the drawings refer to like elements throughout.

FIG. 1 is a diagram illustrating an example of a wearable device worn on a user according to at least one example embodiment.

Referring to FIG. 1, a wearable device 110 is configured to perform a function of assisting a user 100 wearing the wearable device 110 in walking more readily. The wearable device 110 may also be referred to as a walking assist device (WAD) or a gait assist device. When the wearable device 110 is provided to perform such walking assist function, the wearable device 110 may assist or support an entire leg of the user 100 or a portion of the leg to help the user 100 walk more readily. For example, when a person including, for example, a general user and an elderly user, wears the wearable device 110, the wearable device 110 may help the person walk for a longer period of time to enhance an ability of the person to walk or improve an abnormal gait of the person. In addition, the wearable device 110 may provide a force needed for the person to walk, enabling the person to walk independently.

The wearable device 110 may be provided in a wearable exoskeleton type as illustrated in FIG. 1, and configured to assist or support the user 100 to enhance a muscular strength when the user 100 walks and thus to improve a walking movement or a gait of the user 100 or enable the user 100 to walk normally. For example, the wearable device 110 is provided in a hip type that is worn on a hip joint or a thigh as illustrated in FIG. 1. However, a type of the wearable device 110 is not limited to the illustrated example, and other types may also be applicable to the wearable device 110. For example, the wearable device 110 may be provided in a type that assists or supports an entire leg including a hip, a knee, and an ankle, or in a type that assists or supports a portion of the leg, for example, an ankle or a knee.

The wearable device 110 may operate in an exercise mode in which the wearable device 110 provides the user 100 with a resistance force to assist the user 100 in doing an exercise, in addition to a walking assist mode in which the wearable device 110 performs the walking assist function described in the foregoing. The resistance force provided to a body of the user 100 by the wearable device 110 in the exercise mode may act as a force that hinders a movement of the user 100 to increase a muscular strength of the user 100 or help the user 100 be rehabilitated. For example, the wearable device 110 may generate a resistance torque to provide resistance to the user 100 while the user 100 is walking, and apply a resistance force to a movement of the user 100 based on the generated resistance torque.

According to example embodiments to be described hereinafter, the user 100 may do an exercise for at least one lower body muscle that the user 100 desires to strengthen by performing an exercise with the wearable device 110 on in the exercise mode of the wearable device 110. Here, the user 100 may select the lower body muscle, or a lower body part, that the user 100 desires to strengthen, and the wearable device 110 may generate a torque profile to strengthen the lower body muscle selected by the user 100 and may apply a resistance force to a leg of the user 100 in a certain gait segment based on the generated torque profile. The term "gait segment" used herein may refer to a time interval in a gait phase. The user 100 may walk with the wearable device 110 on in the exercise mode, and the wearable device 110 may apply a resistance force to the user 100 in a certain gait segment of a gait phase of the user 100, thereby providing an exercise function to help the user 100 strengthen the lower body muscle selected by the user 100. Through this, it is possible to selectively strengthen a lower body muscle of the user 100, and help the user 100 effectively perform a rehabilitation or an exercise for a certain lower body part. In addition, unlike other exercises, such as, for example, lunge, squat, and cycling, which may also strengthen targeted lower body parts, the walking exercise performed using the wearable device 110 may not strain a joint of the user 100 but have similar exercise effects as those brought by the other exercises.

Figure 2:
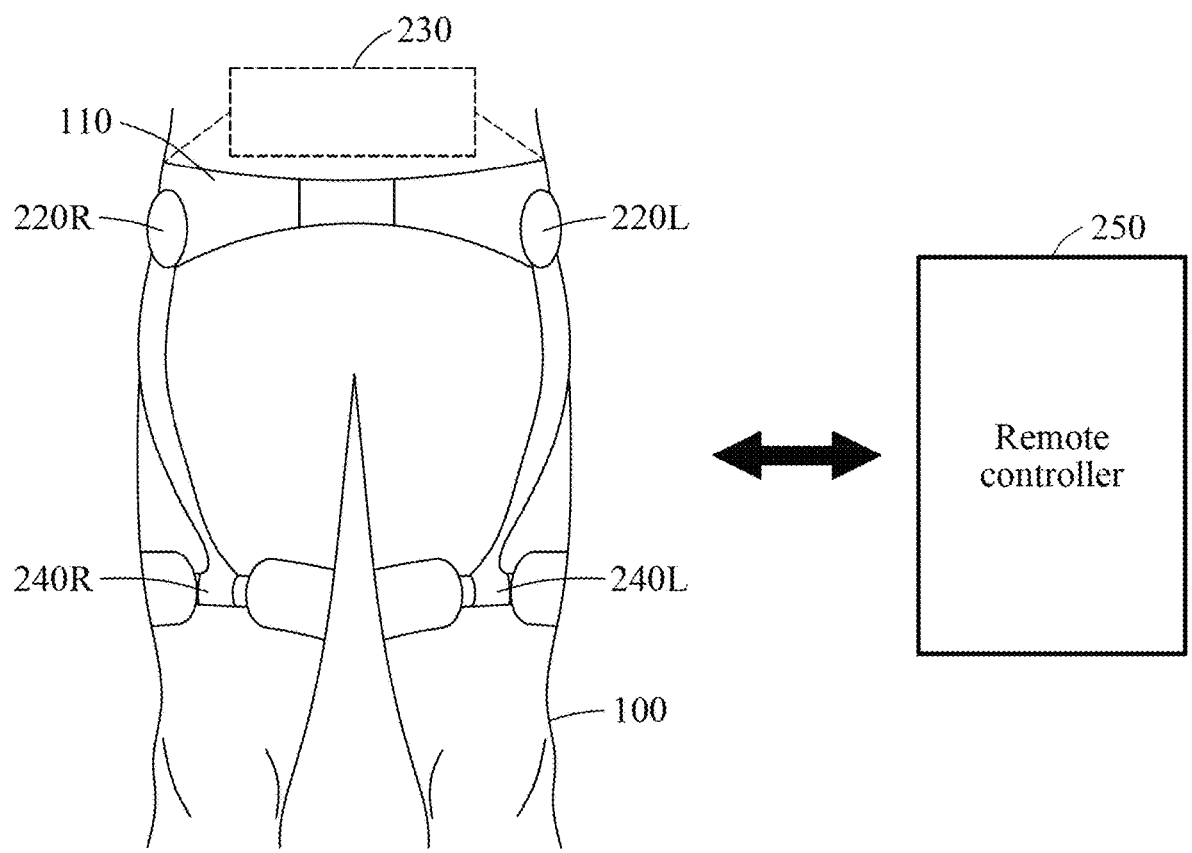
FIG. 2 is a diagram illustrating an example of a structure and a function of a wearable device according to at least one example embodiment.

FIG. 2 is a diagram illustrating an example of a structure and a function of a wearable device according to at least one example embodiment.

Referring to FIG. 2, when a wearable device 110 operates in an walking assist mode, the wearable device 110 generates an assistance torque at left and right hip joint portions 220L and 220R under the control of a controller 230, and the generated assistance torque provides a user 100 wearing the wearable device 110 with an assistance force for extension and/or flexion through transferrers 240L and 240R disposed above knees of the user 100. The wearable device 110 senses a movement of the user 100 through one or more sensors, and estimates a gait phase or a gait state of the user 100 based on information of the sensed movement. The wearable device 110 determines a direction in which an assistance force is to be provided to each of legs of the user 100 at a current time point, and a magnitude of the assistance force to be provided at the current time point, based on the estimated gait phase.

When the wearable device 110 operates in an exercise mode, the controller 230 generates a resistance torque for all segments or one of the segments of the gait phase of the user 100, and the generated resistance torque provides a resistance force which is a force for hindering a leg movement of the user 100 through the transferrers 240L and 240R. The controller 230 determines a torque profile of the resistance torque based on a lower body muscle that is selected by a user input, and operates an actuator of the wearable device 110 based on the determined torque profile. The torque profile includes information associated with a magnitude of a torque to be applied to the actuator and a direction of the torque based on an elapsed time or a progression of the gait phase.

According to an example embodiment, the user 100 selects, through a remote controller 250, a lower body muscle or a lower body part for which the user 100 desires to do an exercise. The user 100 may select the lower body muscle through an interface executed in the remote controller 250. Here, exercise setting information associated with the lower body muscle selected by the user input may be transmitted from the remote controller 250 to the wearable device 110. The controller 230 may then determine the torque profile to be used in the exercise mode based on the exercise setting information received from the remote controller 250. The remote controller 250 may be a mobile device, such as, for example, a personal computer (PC), a laptop, a tablet PC, and a smartphone, a wearable device in other types including, for example, a smart watch, or another electronic device.

According to an example, the exercise setting information may be determined by a user input of a third person, instead of the user input of the user 100 wearing the wearable device 110. The third person may be, for example, a rehabilitation or medical professional or staff, or an assistant who assists the user 100 in walking or doing an exercise.

Figure 3:
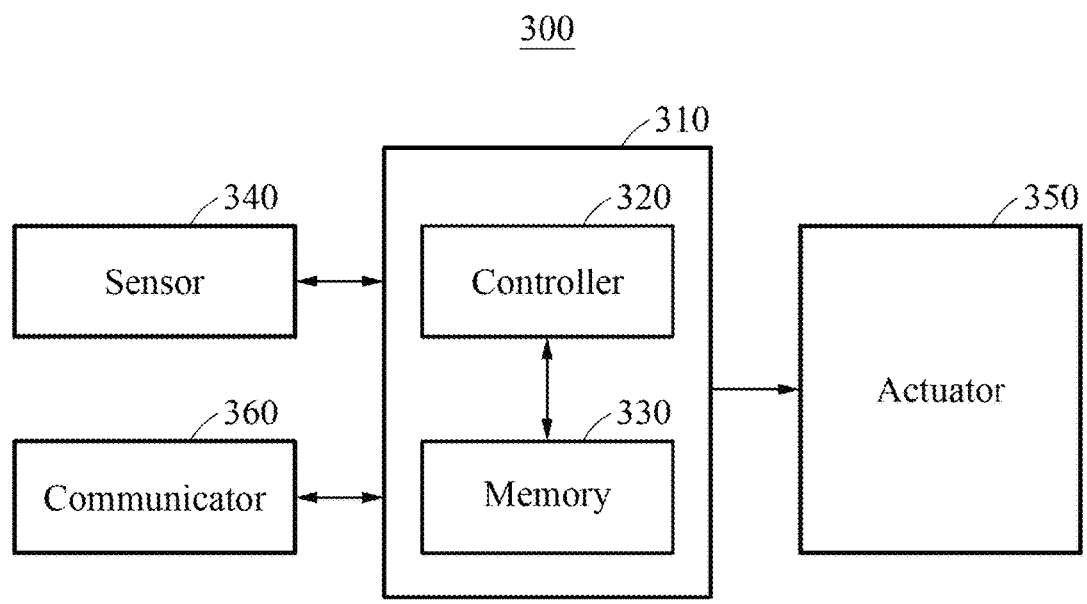
FIG. 3 is a diagram illustrating an example of a configuration of a wearable device according to at least one example embodiment.

FIG. 3 is a diagram illustrating an example of a configuration of a wearable device according to at least one example embodiment.

Referring to FIG. 3, a wearable device 300 includes at least one sensor 340, a control device 310, and an actuator 350. According to an example, the wearable device 300 may further include a communicator 360 configured to communicate with an external device, for example, a remote controller.

The remote controller may control an overall operation of the wearable device 300 in response to a user input. For example, the remote controller may start or stop, or suspend or resume, a function or an operation of the wearable device 300. The remote controller may provide a user interface (UI) that enables an operation or manipulation of the wearable device 300, and a user may control a function and operation of the wearable device 300 through the UI. In addition, through the UI, the user may select a lower body muscle or a lower body part for which the user desires to do an exercise, and select an exercise characteristic including, for example, an exercise intensity and an exercise time. The communicator 360 may receive a control signal for remotely controlling the wearable device 300 from the remote controller, and/or exercise setting information associated with the lower body muscle or the exercise characteristic.

The sensor 340 may include various sensors. For example, the sensor 340 may include a sensor configured to sense or measure a gait phase or a movement of a user wearing the wearable device 300, and a sensor configured to obtain information needed for an operation of the wearable device 300. The sensor 340 may include, for example, an acceleration sensor, an inertial sensor, and/or a gyro sensor to sense a movement of the user and output sensing information therefrom. The sensor 340 may also include, for example, a torque sensor and/or a current/voltage sensor to sense or measure a torque transferred through the actuator 350.

The control device 310 is configured to control an operation and a function of the wearable device 300 and includes a controller 320 and a memory 330. The memory 330 may be connected to the controller 320 and configured to store instructions to be executed by the controller 320, and data to be processed by the controller 320 and/or data having been processed by the controller 320. For example, the memory 330 may store parameters corresponding to a control signal output by the controller 320. The memory 330 may include a non-transitory computer-readable storage medium, for example, a high-speed random-access memory (RAM) and/or a nonvolatile computer-readable storage medium (e.g., at least one disk storage device, flash memory device, or other nonvolatile solid-state memory devices).

The controller 320 may include processing circuitry including, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry may execute instructions that configure the processing circuitry as special purpose processing circuitry that generates a control signal to control the wearable device 300 to set a torque profile such that a resistance torque for hindering a movement of the user wearing the wearable device 300 is output in one or more gait segments corresponding to the lower body muscles selected by the user input. Therefore, the processing circuitry may improve the functioning of the wearable device 300 itself by allowing the wearable device 300 to selectively strengthen selected lower body muscles of the user 100 without the joint strain associated with traditional exercises for strengthening lower body muscles, such as, for example, lunge, squat, and cycling.

For example, the controller 320 may generate a torque control signal to control a torque to be provided by the wearable device 300 based on a movement of the user sensed by the sensor 340. The controller 320 may perform one or more, or all, of operations and functions of a wearable device described herein. The wearable device 300 may operate in one operation mode between a walking assist mode that assists the user in walking and an exercise mode that outputs a resistance torque which is a force for hindering a leg movement of the user. The controller 320 may control an operation and a function of the wearable device 300 according to each operation mode.

According to an example embodiment, the wearable device 300 may receive a user choice input for an operation mode of the wearable device 300. An operation algorithm for each operation mode may be provided in advance in the wearable device 300, and each operation mode may then operate according to the provided algorithm. The controller 320 may operate the wearable device 300 in response to the received user choice input.

When the walking assist mode is selected as the operation mode, the controller 320 may execute an algorithm for determining an assistance force to assist the user wearing the wearable device 300 in walking. For example, the controller 320 may estimate a gait cycle of the user based on sensing information sensed by the sensor 340, and generates a torque control signal based on a gait phase of the user based on the estimated gait cycle.

The actuator 350 may output a torque based on the torque control signal generated by the controller 320. The actuator 350 may provide a force, for example, an assistance force or a resistance force, to a movement of both hip joints of the user. The actuator 350 may convert electrical energy to kinetic energy, and apply the kinetic energy to a body of the user to provide the user with a force needed for the user to move or provide the user with a force that hinders the user from moving. For example, the actuator 350 may be provided as a plurality of actuators, and each of the actuators may be disposed on a portion corresponding to each of positions of the hip joints of the user and generate a torque for flexion and extension of a corresponding leg of the user.

The controller 320 may determine a state variable indicating a gait phase or a gait state of the user based on a walking movement of the user and control the actuator 350 based on the determined state variable. The controller 320 may set a parameter to control the assistance torque based on the state variable and output the torque control signal to assist the user in walking based on the set parameter.

The controller 320 may control the assistance torque to be provided by the wearable device 300 based on the state variable, and determine a control signal to control the assistance torque based on the state variable. The controller 320 may set a gain to adjust a strength of the assistance torque and set a time delay to adjust an output time of the assistance torque. The controller 320 may then define the state variable based on the set gain and the set time delay.

When the exercise mode is selected as the operation mode, the controller 320 may execute an algorithm for determining a resistance force to hinder a movement of the user wearing the wearable device 300. In the exercise mode, the controller 320 may determine a torque profile for a muscular exercise based on a walking exercise of the user, and the actuator 350 may output a torque, for example, a resistance torque, based on the determined torque profile.

For example, the controller 320 may receive exercise setting information associated with a lower body muscle selected by a user input, and determine a torque profile to be applied to the wearable device 300 based on the received exercise setting information. The exercise setting information may include information associated with at least one lower body muscle selected by a user input among lower body muscles of the user.

The user may select at least one lower body muscle for which the user desires to do an exercise and that is set as a target for the exercise, or select all lower body muscles of the user, through an interface provided in the wearable device 300 or the remote controller. The controller 320 may determine a torque profile based on exercise setting information associated with the selected lower body muscles. The exercise setting information may also include information associated with a choice of an exercise intensity. For example, when the user selects a higher exercise intensity, the controller 320 may set the torque profile such that a greater strength of the resistance torque is output.

In some example embodiments, in addition to inputting the aforementioned exercise setting information, the user may also input their body weight, and the controller 320 may adjust the magnitude of torque in the torque profile based on the body weight.

In some example embodiments, the exercise mode may include an initializing mode in which the controller 320 senses the base strength of the muscles of the user to customize an amount of resistance to apply to the user during the exercise mode based on the strength of the user.

In some example embodiments, in addition to inputting the aforementioned exercise setting information, the user may also input an abnormal gait type, and the controller 320 may adjust the torque profile based on the abnormal gait type to compensate for the particular gait abnormality.

In some other example embodiments, rather than the user selecting the at least one lower body muscle to exercise, the controller 320 may automatically select one or more lower body muscles to exercise. For example, in some example embodiments, the controller 320 may randomly select different ones of the lower body muscles to exercise. In other example embodiments, the controller 320 may select the lower body muscles to exercise based on which muscles are most efficiently exercised at a current walking speed of the user. In other example embodiments, the controller 320 may collect historical muscle strength information from the user during prior exercise modes, and may select the lower body muscles to exercise based on the historical muscle strength information indicating, for example, which of the muscles of the user are relatively weak.

Based on the exercise setting information, the controller 320 may set the torque profile such that the resistance torque for hindering a movement of the user wearing the wearable device 300 is output in a gait segment corresponding to the lower body muscle selected by the user input. The controller 320 may estimate the gait phase of the user based on the sensing information obtained from the sensor 340, and determine the torque profile in the exercise mode based on the estimated gait phase and the exercise setting information. For example, the controller 320 may identify the gait segment of the gait phase corresponding to the lower body muscle selected by the user input, and set the torque profile such that the resistance torque is supplied to the actuator 350 in the identified gait segment. As described above, the controller 320 may apply a resistance torque in a suitable gait segment based on a gait phase of the user, and thus assist the user in doing an exercise to strengthen a target lower body muscle that the user desires to strengthen. The controller 320 may adjust a delay in a time point at which a torque is to be applied in the torque profile, and thus adjust a timing of a load to be applied to the user.

According to another example embodiment, the controller 320 may set a torque profile such that an assistance torque and a resistance torque are combined, or the assistance torque and the resistance torque are output simultaneously. For example, the controller 320 may set the torque profile such that the assistance torque for supporting a leg movement of the user wearing the wearable device 300 is output in a first time interval (e.g., 15 minutes) and the resistance torque for hindering a leg movement of the user is output in a second time interval (e.g., 15 minutes). For another example, the controller 320 may set the torque profile such that the assistance torque is output in one gait segment of one gait phase of the user and the resistance torque is output in another gait segment of the gait phase of the user. For still another example, the controller 320 may set the torque profile such that an actuator configured to apply a torque to a right leg of the user outputs the assistance torque and an actuator configured to apply a torque to a left leg of the user outputs the resistance torque, at a same time point.

Figure 4:
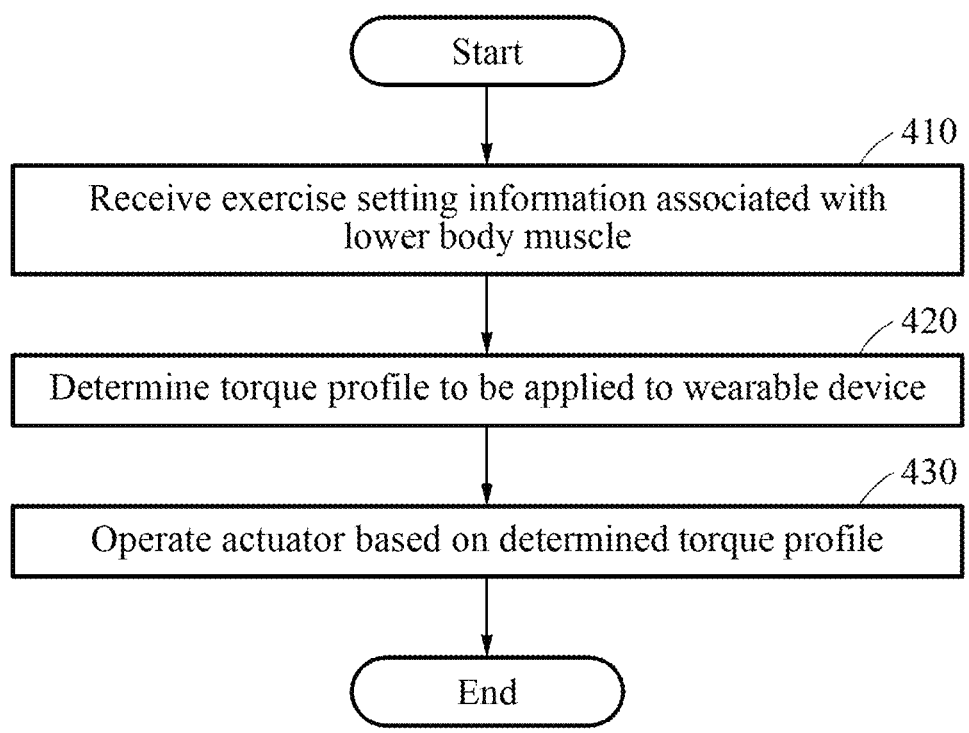
FIG. 4 is a flowchart illustrating an example of an exercise support method performed by a wearable device according to at least one example embodiment.

FIG. 4 is a flowchart illustrating an example of an exercise support method performed by a wearable device according to at least one example embodiment.

As described above, a wearable device may operate in one operation mode (or, alternatively, a combination thereof) between a walking assist mode that assists a user wearing the wearable device in walking, and an exercise mode that outputs a resistance torque which is a force for hindering a leg movement of the user and provides the user with an exercise effect.

Referring to FIG. 4, in operation 410, when the wearable device executes the exercise mode based on a choice made by the user, the wearable device receives exercise setting information associated with a lower body muscle selected by a user input. The exercise setting information may include information associated with at least one lower body muscle that is selected by the user input from among lower body muscles of the user, and exercise intensity information and exercise time information that are selected by the user input. For example, the user may input setting details for a lower body exercise through a remote controller configured to communicate with the wearable device, and the input setting details may be transmitted to the wearable device by being included in the exercise setting information. For another example, the wearable device may include an UI that enables the user to input setting details for a lower body exercise, and the user may determine the exercise setting information through the UI.

In operation 420, the wearable device determines a torque profile to be applied to the wearable device based on the exercise setting information. For example, the wearable device may estimate a gait phase of the user wearing the wearable device based on sensing information sensed by a sensor of the wearable device, and determine the torque profile based on the estimated gait phase and the exercise setting information. The wearable device may determine a resistance torque application interval in which a resistance torque is to be applied according to the exercise setting information based on the gait phase of the user. The wearable device may identify a gait segment of the gait phase corresponding to the lower body muscle selected by the user input, and set the torque profile such that the resistance torque for hindering a movement of the user is supplied to an actuator of the wearable device during the identified gait segment.

In addition, the wearable device may determine a strength of the resistance torque of the torque profile based on an exercise intensity set in the exercise setting information, and set an entire time interval in which the resistance torque is applied.

In operation 430, the wearable device operates the actuator of the wearable device based on the torque profile determined in operation 420. The wearable device may output the resistance torque that hinders a movement of the user through the actuator based on the torque profile. The wearable device may output the resistance torque through the actuator in the gait segment corresponding to the lower body muscle selected by the user input. When the resistance torque is output, the user may strengthen a muscular strength because the user needs to use a greater force or power to move while experiencing a resistance force while the user is doing a walking exercise, compared to when there is no resistance torque applied. In addition, the resistance torque may be output at a time point corresponding to the lower body muscle selected by the user, and thus the user may do an exercise selectively for lower body muscles of the user. Such functions in the exercise mode may be expandable to walking assistance. For example, by assisting or supporting a movement of a hip joint of the user at only a certain time point of gait, it is possible to help a movement of a knee joint or an ankle joint.

Figure 5:
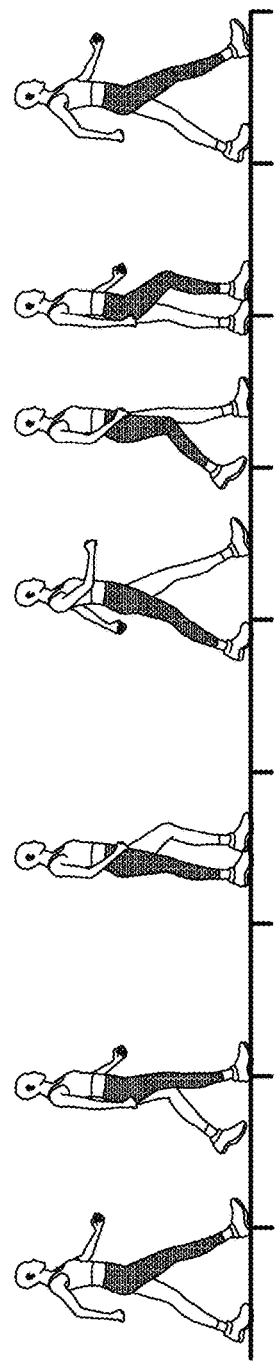
FIG. 5 is a diagram illustrating an example of a change in activation of lower body muscles in a walking exercise process according to at least one example embodiment.
Figure 5:
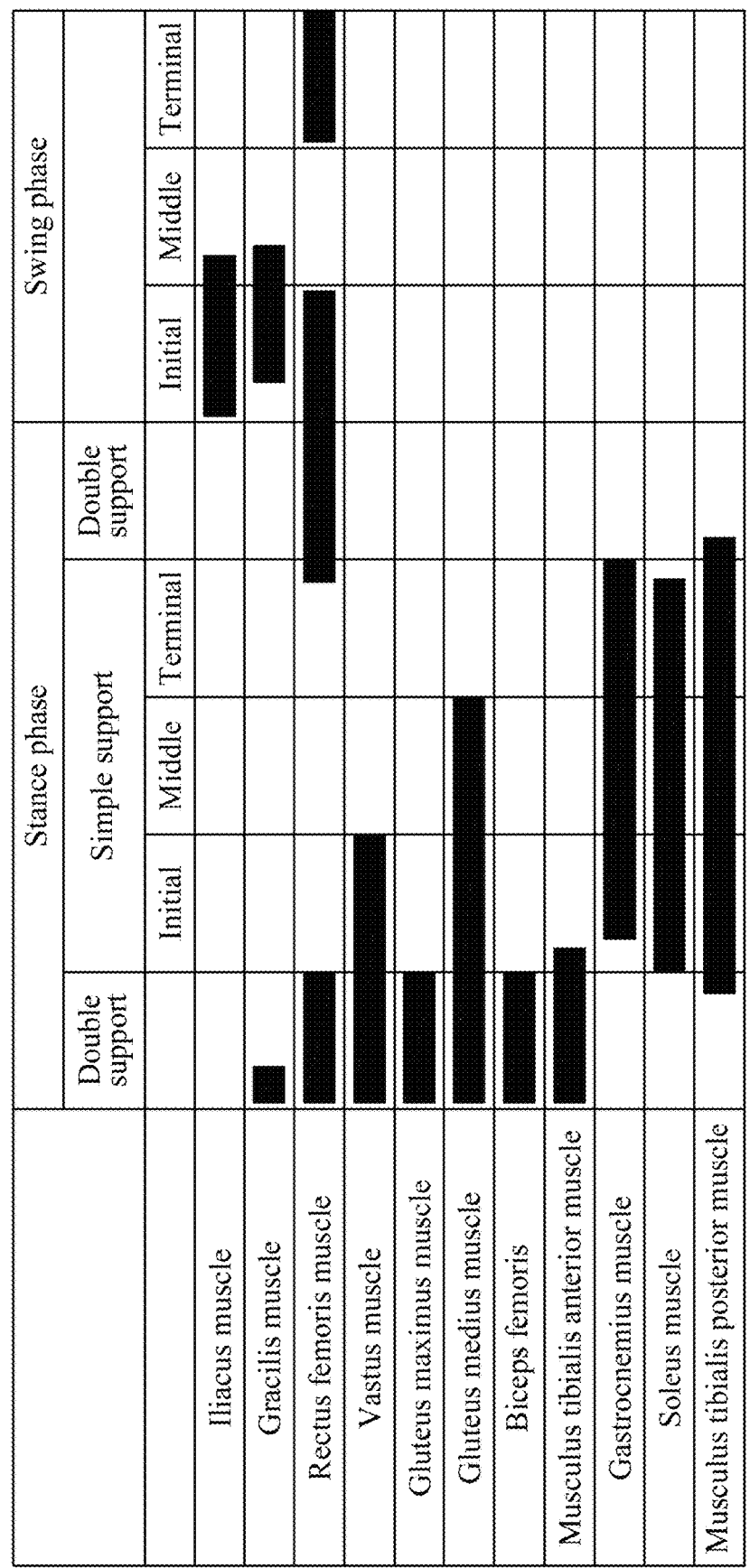

FIG. 5 is a diagram illustrating an example of a change in activation of lower body muscles in a walking exercise process according to at least one example embodiment.

Referring to FIG. 5, a gait phase, or a gait state, may be defined based on one of both legs of a user wearing a wearable device. For example, as illustrated in FIG. 5, the gait phase includes a stance phase and a swing phase based on a right leg of the user. The stance phase may include double support, simple support, and double support in sequential order. The simple support may be subdivided into initial support, middle support, and terminal support. According to a general gait mechanism, a gait phase of each leg may include a stance phase and a swing phase which alternate with each other.

A walking exercise used herein may refer to an exercise that enables the user to strengthen all muscles of a lower body of the user. Referring to a table illustrated in FIG. 5, muscles that are mainly activated in a first double support stage in the stance phase include a gracilis muscle, a rectus femoris muscle, a vastus muscle, a gluteus maximus muscle, a gluteus medius muscle, a biceps femoris, and a musculus tibialis anterior muscle. In addition, muscles that are mainly activated in a simple support stage in the stance phase include a gastrocnemius muscle, a soleus muscle, and a musculus tibialis posterior muscle. In addition, muscles that are activated in the swing phase include an iliacus muscle, the gracilis muscle, and the rectus femoris muscle.

As described above, different lower body muscles may be activated based on a gait phase during a walking exercise process. Thus, in one or more example embodiments, by applying a resistance torque to the user in a segment of a gait phase of the user in which a certain lower body muscle is to be activated, an exercise for strengthening the lower body muscle may be enabled. For example, applying a resistance torque to the right leg of the user wearing the wearable device in a segment corresponding to the simple support of the stance phase may bring a greater effect of an exercise for the gastrocnemius muscle, the soleus muscle, and the musculus tibialis posterior muscle. For another example, applying a resistance torque to the right leg of the user wearing the wearable device in an initial segment of the swing phase may bring a greater effect of an exercise for the iliacus muscle, the gracilis muscle, and the rectus femoris muscle.

Figure 6:
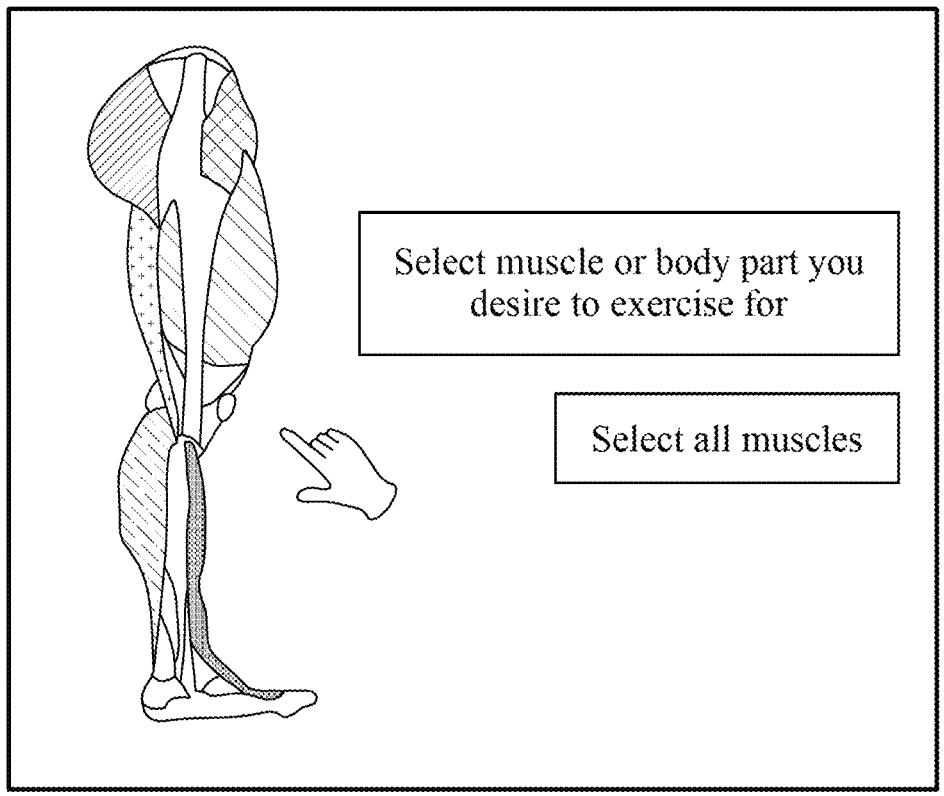
FIG. 6 is a diagram illustrating an example of setting exercise setting information through a user input according to at least one example embodiment.

FIG. 6 is a diagram illustrating an example of setting exercise setting information through a user input according to at least one example embodiment.

According to an example embodiment, a remote controller may provide a UI that enables a user to intuitively set exercise setting information as illustrated in FIG. 6. The remote controller may output shapes and positions of lower body muscles in a form of an image such that the user intuitively recognizes the muscles through the UI.

The user may select, through the UI, at least one lower body muscle or lower body part for which the user desires to do an exercise. For example, the user may select an image of at least one lower body muscle for which the user desires to do an exercise through a touch input. In addition, through the UI, the user may set an exercise intensity or an entire exercise time for the selected lower body muscle. Information associated with details selected and set as described above may be transmitted to a wearable device by being included in exercise setting information.

Figure 7:
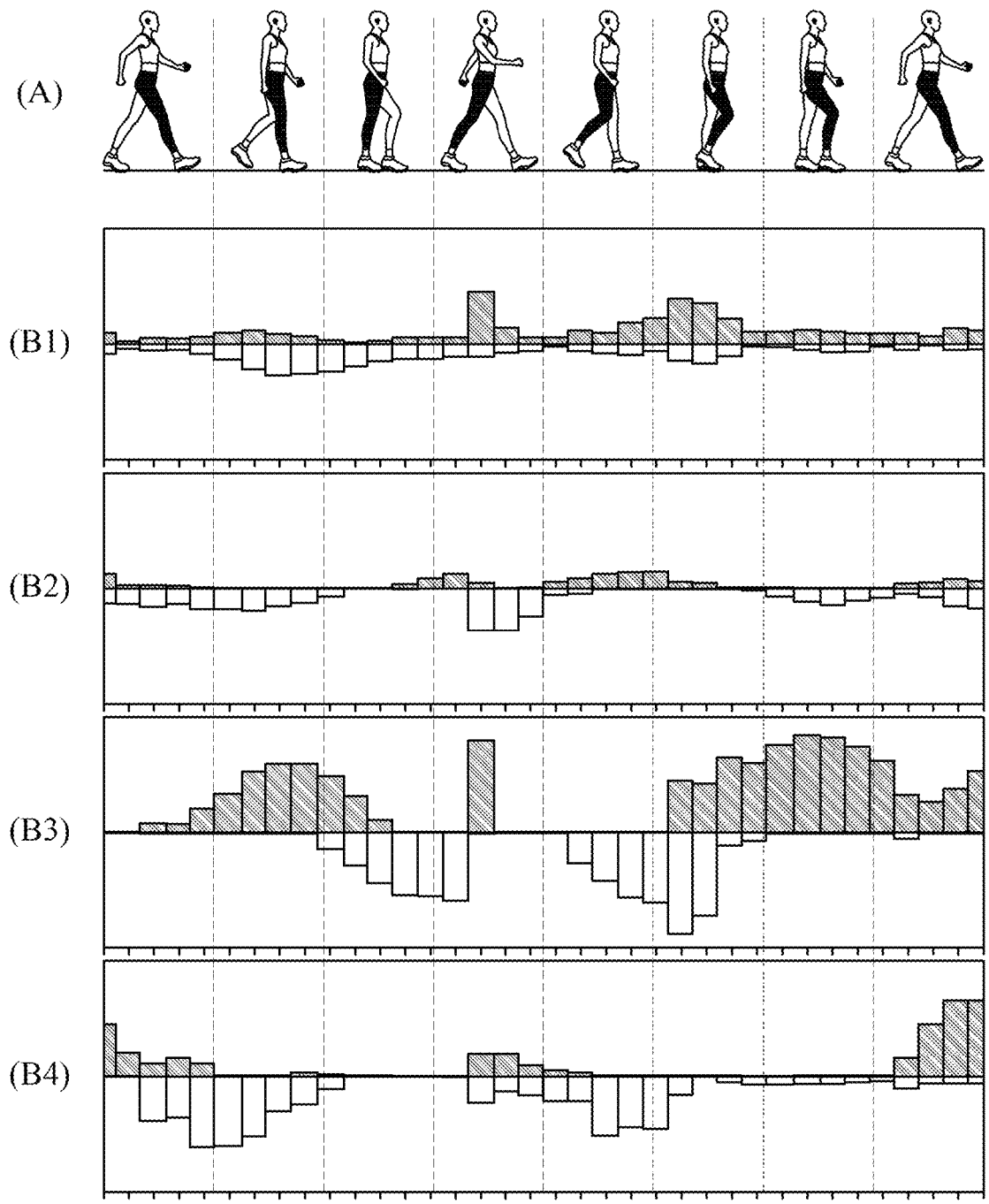
FIG. 7 is a diagram illustrating an example of a change in activation of lower body muscles over time in a walking exercise process according to at least one example embodiment.

FIG. 7 is a diagram illustrating an example of a change in activation of lower body muscles over time in a walking exercise process according to at least one example embodiment.

Referring to FIG. 7, (A) illustrates a flow of a walking process of a user wearing a wearable device. (B1) and (B2) illustrate a change in activation of hip muscles including a gluteus maximus muscle and a gluteus medius muscle based on the flow of the walking process of the user, and a change in activation of hamstrings including a biceps femoris or muscles behind a knee of the user based on the flow of the walking process of the user, respectively. (B3) and (B4) illustrate a change in activation of quadricep muscles before the knee of the user including a rectus femoris muscle based on the flow of the walking process of the user, and a change in activation of ankle muscles including a soleus muscle based on the flow of the walking process of the user, respectively.

(B1), (B2), (B3), and (B4) are muscular activation graphs illustrating changes in activation of muscles that are shown when a resistance torque is not applied to a walking exercise of the user. In the muscular activation graphs, a horizontal axis corresponds to an elapsed time, and a vertical axis indicates a magnitude of activation of muscles. In each of the muscular activation graphs, an upper portion indicates a muscle activation change of a lower body muscle of a left leg of the user, and a lower portion indicates a muscle activation change of a lower body muscle of a right leg of the user.

Figure 8:
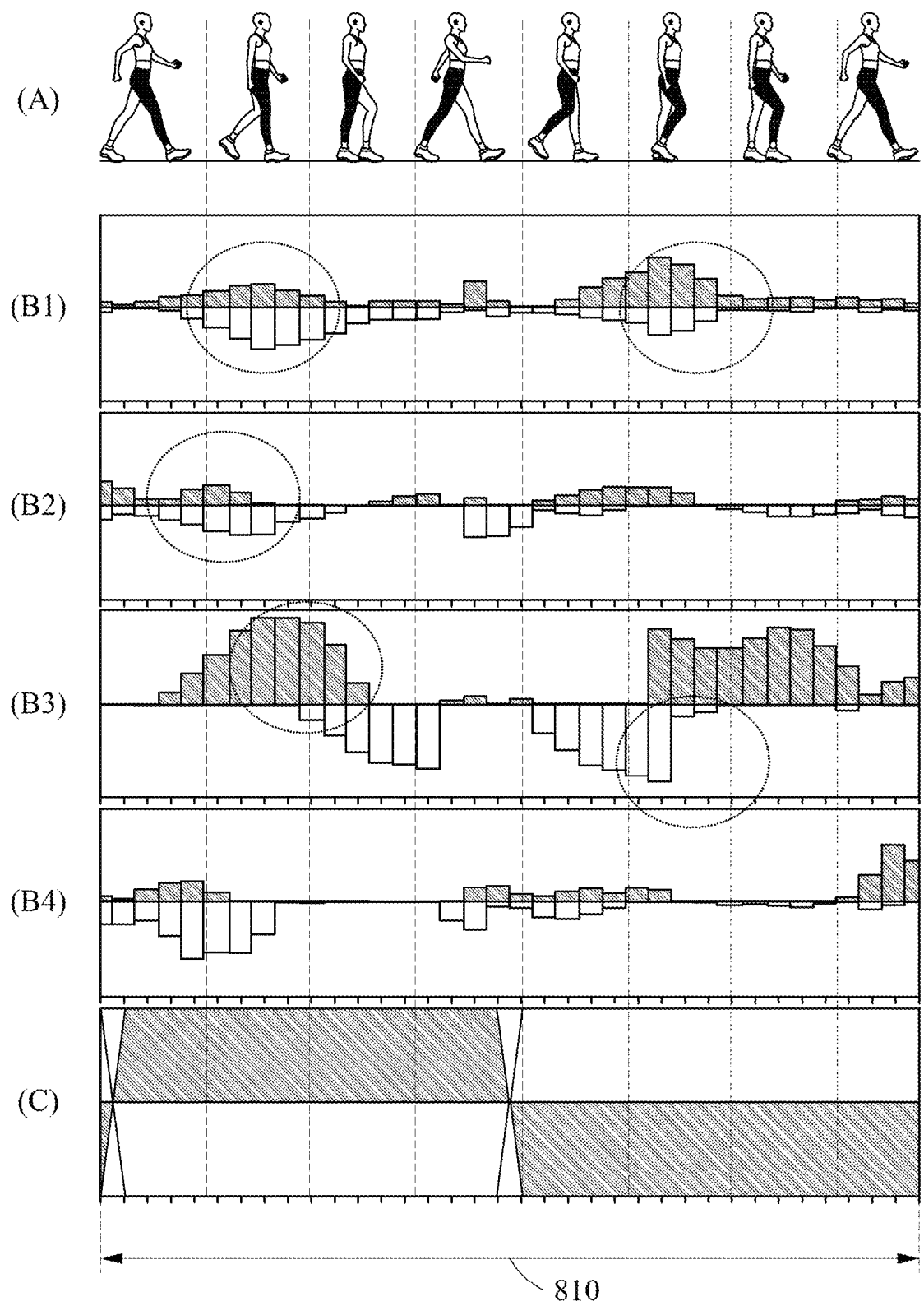
FIG. 8 is a diagram illustrating an example of a change in activation of lower body muscles over time when a resistance torque is applied in all gait segments according to at least one example embodiment.
Figure 9:
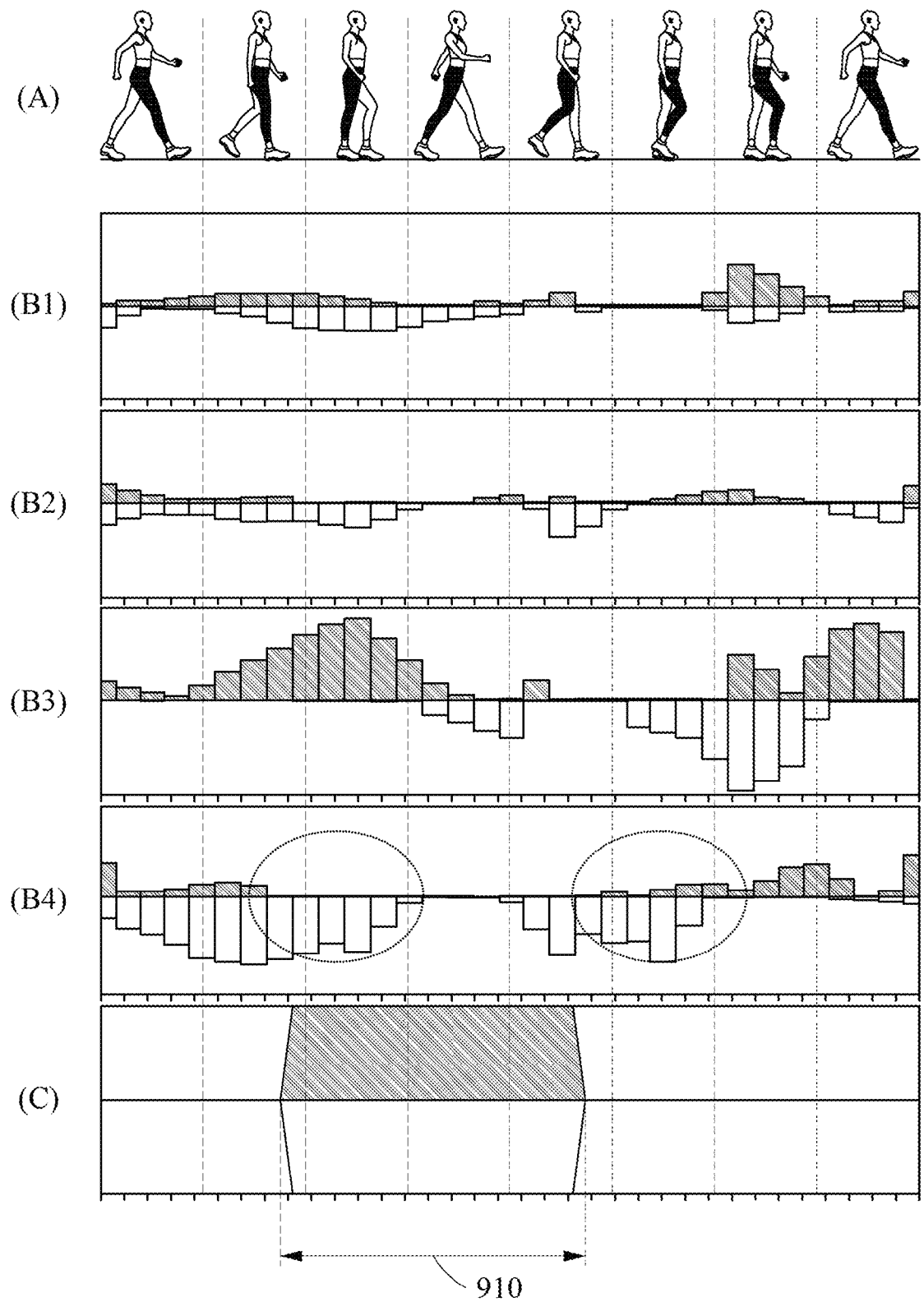
FIG. 9 is a diagram illustrating an example of a change in activation of lower body muscles over time when a resistance torque is applied in some gait segments according to at least one example embodiment.

The description of the muscular activation graphs illustrated in (B1), (B2), (B3), and (B4) may be applicable to muscular activation graphs illustrated in FIGS. 8 and 9.

FIG. 8 is a diagram illustrating an example of a change in activation of lower body muscles over time when a resistance torque is applied in an entire gait segment according to at least one example embodiment.

Referring to FIG. 8, (B1), (B2), (B3), and (B4) illustrate muscular activation graphs of lower body muscles, and (C) illustrates a torque profile to be applied to a wearable device. According to the torque profile, a resistance torque is applied in all gait segments 810. In the torque profile, an upper portion indicates a change in a resistance torque to be applied to an actuator of the wearable device for a left hip joint of a user wearing the wearable device, and a lower portion indicates a change in a resistance torque to be applied to an actuator of the wearable device for a right hip joint of the user.

According to the torque profile, a resistance force may be applied to a movement of the user throughout the user is walking. Thus, as indicated by circles in the muscular activation graphs of FIG. 8, hip muscles, hamstrings muscles behind a knee of the user, and quadricep muscles in front of the knee that are respectively illustrated in (B1), (B2), and (B3) are activated further, compared to the muscular activation changes in a general walking process illustrated in FIG. 7.

When the user desires to strengthen the hip muscles, the muscles behind the knee, and the muscles before the knee during an walking exercise process and selects such muscles, and exercise setting information is determined accordingly, the wearable device may set a torque profile such that a resistance torque is generated in all segments of a gait phase of the user, and thus enable the user to experience an effect of activating the muscles as illustrated in FIG. 8.

FIG. 9 is a diagram illustrating an example of a change in activation of lower body muscles over time when a resistance torque is applied in some gait segments according to at least one example embodiment.

Referring to FIG. 9, (B1), (B2), (B3), and (B4) illustrate muscular activation graphs of lower body muscles, and (C) illustrates a torque profile to be applied to a wearable device. In the torque profile, an upper portion indicates a change in a resistance torque to be applied to an actuator of the wearable device for a left hip joint of a user wearing the wearable device, and a lower portion indicates a change in a resistance torque to be applied to an actuator of the wearable device for a right hip joint of the user wearing the wearable device.

According to the torque profile, a resistance torque is applied in some gait segments 910 among all gait segments corresponding to one gait phase of the user. Thus, a resistance force may be applied to a movement of the user only in the gait segments 910. In such a case, as indicated by circles in the muscular activation graphs of FIG. 9, an ankle muscle illustrated in (B4) is activated further, compared to the muscular activation changes in a general walking process illustrated in FIG. 7.

When the user desires to strengthen the ankle muscle during a walking exercise process and selects such muscle, and exercise setting information is determined accordingly, the wearable device may set a torque profile such that a resistance torque is generated in a time interval corresponding to the gait segments 910 of a gait phase of the user. Thus, as illustrated in FIG. 9, the user may strengthen the ankle muscle through a general walking exercise by doing the walking exercise with the wearable device on. As described above, the wearable device may provide a resistance force to the user at a time point at which each lower body muscle is activated, and thus enable the user to selectively exercise or rehabilitate lower body muscles of the user.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An exercise support method performed by a wearable device, comprising:
   receiving, from a remote controller, exercise setting information comprising information on at least one lower body muscle that is selected by a user input;
   determining a torque profile to apply to the wearable device based on the received exercise setting information; and
   operating an actuator of the wearable device based on the determined torque profile,
   wherein the determining of the torque profile comprises:
   determining one or more gait segments corresponding to the selected at least one lower body muscle among a plurality of gait segments within a gait phase; and
   determining the torque profile such that a resistance torque to hinder a movement of a user is applied in the determined one or more gait segments.

2. The exercise support method of claim 1, wherein the determining of the torque profile comprises:
   determining a resistance torque application interval according to the exercise setting information based on the gait phase of the user,
   wherein the operating the actuator applies the resistance torque during the resistance torque application interval within the one or more gait segments of the gait phase.

3. The exercise support method of claim 1, wherein the exercise setting information further comprises information on an exercise intensity or an entire exercise time for the selected at least one lower body muscle.

4. The exercise support method of claim 1, wherein the determining of the torque profile comprises:
   estimating the gait phase of the user based on sensor information sensed by one or more sensors of the wearable device; and
   determining the torque profile based on the gait phase and the exercise setting information.

5. The exercise support method of claim 1, wherein the determining of the torque profile comprises:
   determining the torque profile such that an assistance torque that supports a leg movement of the user is output in a first time interval and the resistance torque that hinders the leg movement of the user is output in a second time interval.

6. The exercise support method of claim 1, wherein the wearable device is configured to operate in one of a walking assist mode and an exercise mode such that, in the walking assist mode the wearable device assists a leg movement of the user and, in the exercise mode the wearable device outputs the resistance torque to hinder the leg movement of the user.

7. A non-transitory computer-readable medium comprising computer readable instructions that, when executed by a computer, cause the computer to perform the exercise support method of claim 1.

8. The exercise support method of claim 1, wherein the determining of the torque profile comprises:
   determining the torque profile to apply to the wearable device such that the torque profile applies the resistance torque to the selected at least one lower body muscles while not applying the resistance torque in other ones of the plurality of gait segments within the gait phase that do not correspond to the selected at least one lower body muscles.

9. An exercise support method performed by a wearable device, comprising:
   selectively setting the wearable device to an exercise mode;
   receiving, from a remote controller, exercise setting information comprising information on at least one lower body muscle that is selected by a user input in the exercise mode; and
   outputting, via an actuator of the wearable device, a resistance torque,
   wherein the outputting of the resistance torque comprises:
   determining one or more gait segments corresponding to the selected at least one lower body muscle among a plurality of gait segments within a gait phase;
   determining a torque profile such that a resistance torque to hinder a movement of a user is applied in the determined one or more gait segments; and
   outputting the resistance torques through the actuator based on the torque profile.

10. The exercise support method of claim 9, wherein the determining of the torque profile comprises:
    setting the torque profile such that the resistance torque is output in the one or more gait segments corresponding to the selected at least one lower body muscle and the resistance torque is not output in the other ones of the plurality of gait segments within the gait phase that do not correspond to the selected at least one lower body muscle.

11. A wearable device comprising:
    an actuator configured to output a torque based on a torque profile; and
    a controller configured to,
    receive exercise setting information, from a remote controller, the exercise setting information comprising information on at least one lower body muscle that is selected by a user input,
    determine the torque profile based on the received exercise setting information, and
    operate the actuator of the wearable device based on the torque profile,
    wherein the controller is configured to,
    determine one or more gait segments corresponding to the selected at least one lower body muscle among a plurality of gait segments within a gait phase, and
    determine the torque profile such that a resistance torque to hinder a movement of a user is applied in the determined one or more gait segments.

12. The wearable device of claim 11, wherein the controller is configured to,
    set the torque profile such that the resistance torque to hinder a movement of the user is output in the one or more gait segments corresponding to the selected at least one lower body muscles.

13. The wearable device of claim 11, further comprising:
    a sensor configured to sense a movement of the user to generate sensing information,
    wherein the controller is configured to,
    estimate the gait phase of the user based on the sensing information, and
    determine the torque profile based on the gait phase and the exercise setting information.

14. The wearable device of claim 11, wherein the controller is configured to determine the torque profile such that an assistance torque that supports a leg movement of the user is output in a first time interval and the resistance torque that hinders the leg movement of the user is output in a second time interval.

15. The wearable device of claim 11, the wearable device is configured to operate in one of a walking assist mode and an exercise mode such that, in the walking assist mode the wearable device assists a leg movement of the user and, in the exercise mode the wearable device outputs the resistance torque to hinder the leg movement of the user.

16. The wearable device of claim 11, further comprising:
a communicator configured to receive the exercise setting information from the remote controller.

17. The wearable device of claim 11, wherein the controller is configured to,
determine the torque profile to apply to the wearable device such that the torque profile applies the resistance torque to the selected at least one lower body muscles while not applying the resistance torque in other ones of the plurality of gait segments within the gait phase that do not correspond to the selected at least one lower body muscle.

18. The wearable device of claim 11, wherein the exercise setting information further comprises information on an exercise intensity or an entire exercise time for the selected at least one lower body muscle.

\* \* \* \* \*